United States Patent [19]

Gain

[11] Patent Number: 4,590,164

[45] Date of Patent: May 20, 1986

[54] PROCESS FOR THE PREPARATION OF A GLUCOSE-FREE HEMOGLOBIN STANDARD

[75] Inventor: Thomas Gain, Munich, Fed. Rep. of Germany

[73] Assignee: Panchem GmbH, Kleinwallstadt, Fed. Rep. of Germany

[21] Appl. No.: 593,127

[22] Filed: Mar. 26, 1984

[30] Foreign Application Priority Data

Mar. 29, 1983 [DE] Fed. Rep. of Germany ....... 3311458

[51] Int. Cl.$^4$ .................. G01N 31/00; A01N 1/02; C12Q 1/26; C12N 9/96
[52] U.S. Cl. .................................. 436/15; 436/16; 436/17; 436/18; 424/101; 435/2; 435/25; 435/26; 435/188
[58] Field of Search .................... 436/13, 15, 16, 17, 436/66, 67, 71; 424/101; 435/2, 25, 26, 188; 422/61

[56] References Cited

U.S. PATENT DOCUMENTS

| | | | |
|---|---|---|---|
| 3,607,695 | 9/1971 | Pfizer | 436/15 |
| 3,964,865 | 6/1976 | Das | 436/15 |
| 4,465,774 | 8/1984 | Huang et al. | 436/15 |
| 4,485,174 | 11/1984 | Chiang et al. | 436/15 |

*Primary Examiner*—Thomas Wallen
*Attorney, Agent, or Firm*—Burns, Doane, Swecker & Mathis

[57] ABSTRACT

A process for the preparation of a glucose-free glycosylated hemoglobin standard in which hemoglobin with a known content of glycosylated hemoglobin $HbA_{Ia+b+c}$ is converted to cyanmethemoglobin by means of a $K_3(FeCN)_6/KCN$ solution, stabilized with a sodium phosphate-cyanide buffer and preserved by lyophilizing at −40° C. with a subsequent increase in temperature to −20° C. under a high vacuum and stored at this temperature with the exclusion of light, whereupon the glucose-free glycosylated hemoglobin standard may be reconstituted by the addition of an aqueous medium.

9 Claims, No Drawings

PROCESS FOR THE PREPARATION OF A GLUCOSE-FREE HEMOGLOBIN STANDARD

BACKGROUND OF THE INVENTION

For the control of the metabolism of diabetic patients the determination of glycosylated hemoglobins in diabetic surveillance has proved to be an informative and reliable process in clinical practice, in addition to the determination of blood and urine sugars.

Hemoglobin, the pigment of the blood corpuscles, consists of approximately 5% of a coloring component, the heme, and approximately 95% of a protein, the globin, which are bonded together in the manner of a complex.

It has now been found that in the column chromatographic separation of hemoglobin solutions the principal hemoglobin portion, namely $HbA_I$, is inhomogeneous, i.e., in front of the main fraction a series of more rapidly migrating hemoglobins, designated $HbA_1$, were eluted. These hemoglobin fractions may be separated into the components $HbA_{Ia}$, $HbA_{Ib}$ and $HbA_{Ic}$. Chemical structure determinations showed that glycoproteins, i.e., glycosylation products of hemoglobin $A_I$ are involved, formed by a condensation reaction of tne aldehyde group of carbohydrate molecules, such as fructose-1,6-diphosphate, glucose-6-phosphate and glucose with terminal amino groups. An equilibrium reaction initially leads to the formation of the unstable aldimine (Schiff's base), which by way of an amadorium orientation leads irreversibly to the ketoamine. The glycosylated hemoglobin ($HbA_{Ia}$, $HbA_{Ib}$ and $HbA_{Ic}$) is formed in a non-enzymatic reaction during the life of the erythrocytes of approximately 120 days.

While in persons without diabetes and with a healthy metabolism and proportion of glycosylated hemoglobin is between 3.5 and 7.5%, in the case of diabetic patients it may be increased to 20% and more, with respect to the total Hb.

U.S. Pat. No. 3,964,865 discloses a lyophilized hemoglobin standard for the colorimetric determination of total hemoglobin, prepared by filtering a "crude" hemoglobin fraction wherein by means of the atmospheric oxygen introduced by the filtration, the hemoglobin is oxidized to methemoglobin, i.e., to oxyhemoglobin. After adjustment to a predetermined concentration value, the methemoglobin is lyophilized and is suitable in this form as a standard agent for the colorimetric determination of total hemoglobin. In order to comply with the standards established by the National Academy of Sciences—National Research Council, USA (NRC) and the International Committee for Standardization in Haematology (ICSH), the lyophilized standard is converted to cyanmethemoglobin prior to use.

However, with this state of the art standard, only a spectroscopic determination of the total hemoglobin is possible, but not a determination of individual hemoglobin fractions, such as for example the $HbA_I$ fraction, since in the oxidation of hemoglobin to methemoglobin both the prosthetic groups and the orientation behavior of the chains are altered, so that such a standard exhibits for example a chromatographic behavior other than that of untreated blood and therefore cannot be used either for a direct determination of hemoglobin fractions nor as a standard for the correct handling of the separation process chosen for example for the determination of $HbA_I$.

For the determination of the proportion of glycosylated hemoglobin in the total hemoglobin, different processes are available. In view of the stronger negative charge of glycosylated hemoglobins $HbA_I$, the latter may be separated from other hemoglobins by means of ion exchange chromatography, high pressure liquid chromatography and electro-osmosis. A further method for the determination of glycosylated hemoglobins is based on the hydrolysis of the glycosylated hemoglobins in oxalic acid and conversion of the hexoses split off to 5-hydroxymethylfurfural, which after reaction with thiobarbituric acid (TBA) may be measured photometrically. An affinity chromatographic separation, using the hydroxyl groups of the carbohydrates bound to the hemoglobin, is also possible.

The use of the different methods of determination leads, however, to the disadvantage that the analytical results obtained with the same sample correlate differently with each other, depending on the method applied. Thus, for example, regardless of whether macro- or microcolumns are used for the proportional content of glycohemoglobin, the $HbA_I$ values found by the chemical TBA method are comparable by means of a correction factor only. Furthermore, in the usual analytical processes in part the total $HbA_I$ fraction and the separated individual $HbA_{Ia,b}$ and $HbA_{Ic}$ fractions are determined, so that analytical values cannot be given uniformly and are therefore difficult to compare with each other. If, for example, the glycosylated hemoglobin components $HbA_{Ia+b+c}$, which are readily determined both by conventional macrocolumn chromatography and by high pressure liquid chromatography, are analyzed, the evaluation of the results merely shows a correlation but no agreement between the two methods.

In summary, it may be stated that the individual methods for the determination of glycosylated hemoglobins, in particular ion exchange chromatography, yield good results with respect to the separation of the fractions, but that these results are not, depending on the process used, transferable and thus comparable. For the internal control of specific separation methods at the present time standard controls are used, which are applicable to a certain process only. However, the comparability of all of the separation techniques applied and thus of the values found by means of a universal standard remains an important requirement of routine clinical examinations.

It is the object of the present invention to provide a process for the preparation of a stable glycosylated hemoglobin standard to make possible the quality control of the $HbA_I$ determination by all of the separation method used; both internally and externally with an identical material.

This object is attained in the process according to the present invention.

SUMMARY OF THE INVENTION

The present invention is a method for producing a glucose-free hemoglobin standard. In the method, an aliquot of erythrocytes are washed with an isotonic salt solution and then hemolyzed. The free and glycosylated hemoglobins in the hemolysate are converted to the corresponding cyanmethemoglobins by use of a dilute $K_3[Fe(CN)_6]$ solution and a dilute KCN solution, and then a suitable buffer is added. The lipids and cellular remnants are removed by a suitable solvent, the hemolysate is desalted, and then lyophilized.

DETAILED DESCRIPTION OF THE INVENTION

The process for the preparation of a stable glycosylated hemoglobin standard is based on the conversion of hemoglobin to cyanmethemoglobin. The cyanmethemoglobins prepared according to the invention retain a constant extinction ratio even during an extended storage period, while the extinction ratios of differently substituted hemoglobins do not remain Hb variant specific during extended storage, and are therefore not suitable as standard controls.

It has been found to be especially advantageous for the successful preparation of the glycosylated hemoglobin standards of the present invention to wash the erythrocytes several times with a dilute isotonic NaCl solution before the hemolysis, prior to the conversion of the free hemoglobin and the glycosylated hemoglobin into the corresponding cyanmethemoglobins, and subsequently to stabilize the hemolysate with a Na phosphate-cyanide buffer, since at the result of this measure the $K_3[Fe(CN)_6]$ complex, which otherwise is unstable under the reaction conditions, on the one hand retains its oxidizing effect and on the other, causes no undesirable reactions on the globin chains. In place of the masking CN ions, for example SCN ions may also be used.

For the clean removal of cell remnants and lipids, it has been found to be favorable, to treat the hemolysate advantageously subsequently with $CCl_4$. In place of $CCl_4$, for example a different fat solvent, such as toluene, etc., may be used, but it must otherwise be inert with respect to the hemoglobin.

If the hemoglobin standards according to the invention are not used immediately after their preparation, they are lyophilized in a high vacuum by freezing initially at low temperatures with a subsequent slow rise in temperature, in a very gentle manner. This process is particularly important as the protein content of the hemoglobin must not be denaturated in order not to endanger the ability of the hemoglobin standard to function as a quality control in the determination of $HbA_I$. Quality controls prepared in this manner may be preserved for at least 8 months under refrigeration and with the exclusion of light.

With respect to the TBA method it should be emphasized particularly that the glycohemoglobin standards prepared by the newly developed process contain no unbonded glucose, as the latter is no longer needed to stabilize the equilibrium and no cleavage of the glycosylated hemoglobins occurs during their preparation and storage. This prevents the indication of higher values by the TBA method as the result of the otherwise non-specifically increased 5-hydroxymethyl-furfural formation.

In order not to reduce the solubility of the hemoglobin standards by a salting-out effect, thereby leading in certain methods to false indications concerning the hemoglobin components, desalting is effected according to the invention, for example by gel filtration or dialysis.

By the addition of aqueous media the lyophilized hemoglobin standards may be reconstituted very rapidly and simply for use in quality control as needed.

The following example describes the process according to the invention for the preparation of a stable, glucose-free glycosylated hemoglobin standard.

To obtain a more complete understanding of the present invention, the following example is set forth. However, it should be understood that the invention is not limited to the specific details set forth in the following example.

EXAMPLE

Initially, one ml of erythrocytes is washed three times with 20 ml of an isotonic NaCl solution, with the supernatant liquid being suctioned off in each case after centrifuging. One ml distilled water is then added for the hemolysis and the solution allowed to stand for 2 minutes. The conversion of the hemoglobin to cyanmethemoglobin is effected by the addition of 80 $\mu$l of a 5% $K_3[Fe(CN)_6]$ solution and 2 ml of a 0.5% KCN solution, standing for 2 minutes in each case, and repeated vigorous mixing. The hemolysate is subsequently diluted with 12 ml of a Na phosphate-cyanide buffer at approximately 6.7 pH. This pH value is usually attained by dissolving 4.59 g $NaH_2PO_4 \times H_2O$ and 1.18 g $Na_2HPO_4$ and 0.65 g of KCN with distilled water in a total volume of 1 l. To remove the lipids and cellular remnants, 2 ml $CCl_4$ are then added and the mixture centrifuged for 10 minutes. Subsequently, desalting is performed by conventional methods, for example by gel filtration or dialysis.

The initial solution described above yields approximately 24 standards. For their preservation, the standards are lyophilized in a high vacuum at $-40°$ C. and a subsequent increase in temperature to $-20°$ C. for 48 hours.

It has been found that the stability of the standards is assured for at least 8 months when kept under refrigeration in the dark. The quality controls are used after reconstitution by the addition of 0.5 to 0.2 ml, respectively, of preferably distilled water. The total hemoglobin content of the standard in the aforesaid sample is between 4 and 6 mg per 0.5 ml. The exact determination is effected in the usual manner.

The standards prepared by the process according to the invention may be used in all methods for the determination of glycosylated hemoglobins with consideration of their specific method of detection and standard ranges, so that for the first time a universal standard is available for the determination of the $HbA_I$ fraction of hemoglobin.

This is illustrated in Table 1 below.

TABLE 1

Determination of glycosylated hemoglobins by means of different separation methods of an identical charge with 10 determinations using a hemoglobin standard according to the invention.

| Method of Determination | % $HbA_{Ia+b}$ | % $HbA_{Ic}$ | % $HbA_{Itot.}$* |
|---|---|---|---|
| Macrocolumn | 3.8 | 6.9 | 10.7 |
| High pressure liquid chromatography (HPLC) | 3.6 | 6.7 | 10.3 |
| TBA | | 6.4 | |
| Affinity chromatography | | | 11.3 |
| Microcolumn | | | 9.8 |
| Electro-osmosis | | | 7.3 |
| Isofocusing | 2.8 | 4.2 | 7.0 |

Note:
The percentage values of the glycosylated hemoglobin fractions given are relative values with respect to the total hemoglobin.
*% $HbA_{Itot.}$ = $HbA_{Ia+b}$ + $HbA_{Ic}$.

As seen in Table 1, the use of the hemoglobin standards according to the invention with different but comparable separation methods, such as high pressure liquid chromatography (HPLC), macrocolumn, microcolumn and the thiobarbituric acid method—comparable after correction by a certain correction factor with the separating column method—yields results that are within the expected error limits inherent in the system, so that the employment of the hemoglobin control standards according to the invention as a control of the accuracy of the $HbA_I$ determination methods used for the determination of the metabolic condition of diabetic patients is of universal importance.

Even the value found by the recently introduced affinity chromatographic method is within the same order of magnitude, as expected.

The use of the hemoglobin standards as controls permits the establishment of confirmation of whether the separation system has been handled correctly even with separation methods such as isofocusing and electro-osmosis which are not comparable with the aforecited methods in view of their different hemoglobin fraction separation mechanisms.

As seen in Table 1, in this case values of the $HbA_I$ component lower by approximately 7% are obtained, but these are within the range of the results expected with this method, in view of the values found with the other methods. Similar proportions are further observed in comparative measurements with untreated blood of identical composition.

While the separation of the total fraction $HbA_{Itot}$ into the individual fractions $HbA_{Ia+b}$ and $HbA_{Ic}$ is not of great importance in practical examinations, these fractions may also be tested for accuracy with the new glycosylated hemoglobin standards, independently of the separation method, in particular HPLC, TBA, macrocolumn and isofocusing.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:
1. A process for the preparation of a glucose-free hemoglobin standard comprising the steps of:
   (a) washing an aliquot of erythrocytes with an isotonic salt solution,
   (b) hemolyzing the erythrocytes to produce a hemolysate containing free and glycosylated hemoglobins,
   (c) converting the free and glycosylated hemoglobins in the hemolysate into the corresponding cyanmethemoglobins by use of a dilute $K_3[Fe(CN)_6]$ solution and a dilute KCN solution,
   (d) adding a Na phosphate-cyanide buffer to stabilize the hemolysate from step (c),
   (e) removing the lipids and cellular remnants from the stabilized hemolysate of step (c) by use of an inert solvent,
   (f) desalting the hemolysate obtained from step (e), and
   (g) lyophilizing the hemolysate obtained from step (f).
2. The process of claim 1 wherein the isotonic salt solution of step (a) is an isotonic NaCl solution.
3. The process of claim 1 wherein the hemolysis of step (b) is performed using distilled water.
4. The process of claim 1 wherein the solvent of step (e) is $CCl_4$ or toluene.
5. The process of claim 1 wherein the desalting of step (f) is performed by gel filtration or dialysis.
6. The process of claim 1 wherein the lyophilizing of step (g) is performed in a high vacuum at $-40°$ C.
7. The glucose-free hemoglobin standard prepared by the method of claim 1.
8. The standard of claim 7 which has been reconstituted by the addition of distilled water.
9. The process of claim 1 wherein the buffer added in step (d) has a pH of approximately 6.7.

* * * * *